US006832400B2

(12) United States Patent
Loveday, III et al.

(10) Patent No.: US 6,832,400 B2
(45) Date of Patent: Dec. 21, 2004

(54) PATIENT HANDLING SYSTEM AND ASSOCIATED PALLET MOUNTING APPARATUS

(75) Inventors: George E. Loveday, III, Knoxville, TN (US); Franck Picker, Oak Ridge, TN (US)

(73) Assignee: CTI PET Systems, Inc., Knoxville, TN (US)

( * ) Notice: Subject to any disclaimer, the term of this patent is extended or adjusted under 35 U.S.C. 154(b) by 29 days.

(21) Appl. No.: 10/325,315

(22) Filed: Dec. 19, 2002

(65) Prior Publication Data

US 2004/0117910 A1 Jun. 24, 2004

(51) Int. Cl.[7] .................................................. A61B 6/04
(52) U.S. Cl. ................................ 5/601; 5/620; 378/209
(58) Field of Search ..................... 5/601, 620; 378/209; 108/158.12, 159, 157.1, 157.15

(56) References Cited

U.S. PATENT DOCUMENTS

| | | | | |
|---|---|---|---|---|
| 3,065,344 A | * | 11/1962 | Chervenka | 378/177 |
| 4,727,328 A | * | 2/1988 | Carper et al. | 324/318 |
| 4,795,142 A | * | 1/1989 | Schaefer | 5/620 |
| 5,077,780 A | * | 12/1991 | Lee, Jr. | 378/196 |
| 5,199,123 A | * | 4/1993 | Jacques et al. | 5/601 |
| 5,983,424 A | * | 11/1999 | Naslund | 5/601 |

* cited by examiner

Primary Examiner—Michael Trettel
(74) Attorney, Agent, or Firm—Pitts & Brittian, PC

(57) ABSTRACT

A patient handling system (10) for use with a medical imaging or radiation therapy device, and an associated pallet mounting apparatus (12) for releasably mounting a pallet (18) on the pallet support assembly (16) of a patient handling system. The patient handling system (10) includes a pallet (18) for supporting a patient, and a pallet support assembly (16) for supporting the pallet (18) and for positioning the pallet (18) to facilitate the scanning of a patient positioned on the pallet (18) using the medical imaging device, or to facilitate the application of radiation therapy to a patient using a radiation therapy device. The pallet mounting apparatus (12) includes a first interlocking member, or base member (32), mounted on the pallet support assembly (16), and a second interlocking member, or pallet engaging member (34), mounted on the pallet (18) for releasably interlocking with the base member (32), whereby selective vertical pivoting of the pallet engaging member (34) relative to the base member (32) permits selective disengagement of the pallet engaging member (34) from the base member (32) to facilitate release of the pallet (18) from the pallet support assembly (16).

18 Claims, 8 Drawing Sheets

PATIENT HANDLING SYSTEM AND ASSOCIATED PALLET MOUNTING APPARATUS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention relates to patient handling devices in the field of Positron Emission Tomography (PET), Computed Tomography (CT) and other related imaging and therapy devices. More specifically, the present invention is related to a patient handling system, and an associated apparatus for releasably mounting a pallet on which a patient is positioned during an imaging or radiation therapy procedure.

2. Description of the Related Art

In the field of medical imaging and radiation therapy, it is well known that patients are positioned on the bed or pallet of a patient handling system which allows the patients to be moved into position within a field of view of a plurality of detectors, or into the targeting area of a radiation emitting device. Such patient handling systems typically include a pallet support assembly which supports the pallet in the desired horizontal orientation. In order to facilitate the movement of the patient into the field of view of the detectors or emitting device, some patient handling systems are provided with mechanisms for moving the pallet into, and out of, the field of view of the detectors, or the radiation targeting area, while the pallet support assembly remains stationary. In some patient handling systems the pallet support assemblies are moveable, such that the entire patient handling system is moved to accommodate the positioning of the patient within the field of view or the targeting area of the imaging or therapy device. In both types of patient handling systems the pallet on which the patient is positioned is typically bolted to a component of the pallet support assembly, or otherwise fixedly secured, such that the pallet cannot be readily removed from the pallet support assembly.

Fixedly securing the pallet to the pallet support assembly is advantageous in that it ensures that there is no inadvertent movement of the pallet during the imaging or therapy process which would compromise the accuracy or efficacy of the procedure being performed. However, different imaging or therapy procedures can require different pallet configurations. For example, for many PET applications a pallet having a concaved patient support surface may be desirable, while for radiation therapy applications a pallet having a flat patient support surface may be desirable. Where pallets are fixedly secured to the pallet support assembly of the patient handling system it may be difficult and/or time consuming, and in some circumstances impossible, to interchangeably use pallets having different configurations with the same patient handling system. As a result, different patient handling systems carrying different pallets may be necessary for procedures with different types of imaging or therapy devices, and different patient handling systems having pallets with different configurations may be necessary for different medical procedures using the same imaging or therapy device.

BRIEF SUMMARY OF THE INVENTION

The present invention provides a patient handling system and associated apparatus for releasably mounting a pallet for supporting a patient during a medical imaging or radiation therapy procedure. The patient handling system includes a pallet for supporting a patient, and a pallet support assembly for supporting the pallet and for positioning the pallet to facilitate the scanning of, or the application of radiation therapy to, a patient positioned on the pallet. The pallet mounting apparatus includes a first interlocking member, or base member, mounted on the pallet support assembly. The apparatus also includes a second interlocking member, or pallet engaging member, mounted on the pallet for releasably interlocking with the base member, whereby the selective vertical pivoting of the pallet engaging member relative to the base member permits selective disengagement of the pallet engaging member from the base member to facilitate release of the pallet from the pallet support assembly. In one embodiment of the invention the pallet engaging member of the pallet mounting apparatus is provided with a pair of downwardly extending detention arms which are releasably received in detention arm receptors provided in the base member of the pallet mounting apparatus. In another embodiment, the patent engaging member of the apparatus is provided with a pair of receptors which releasably engage the base member of the pallet mounting apparatus. From the detailed description which follows it will be recognized that the present invention has great advantages over the prior art by providing a patient handling system wherein pallets of different configurations can be used with the same system, and wherein the releasably mounted pallets are held firmly in position such that a patient can be safely positioned on the pallet without the risk that the pallet will disengage. In this regard, the mechanical interlock of the present invention is designed such that the patient load on the pallet secures the pallet in place. In order to disengage the pallet from the pallet support assembly the distal end of the pallet must be pivoted upwardly and the pallet lifted from the support assemble. Therefore, the pallet will not inadvertently disengage while a patient is in position on the pallet. This notwithstanding, the pallet can be easily disengaged without the use of tools when a patient is not positioned on the pallet. Further, the secure positioning of the pallet on the pallet support assembly insures that the medical imaging or radiation therapy procedure is not compromised by inadvertent movement of the pallet.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
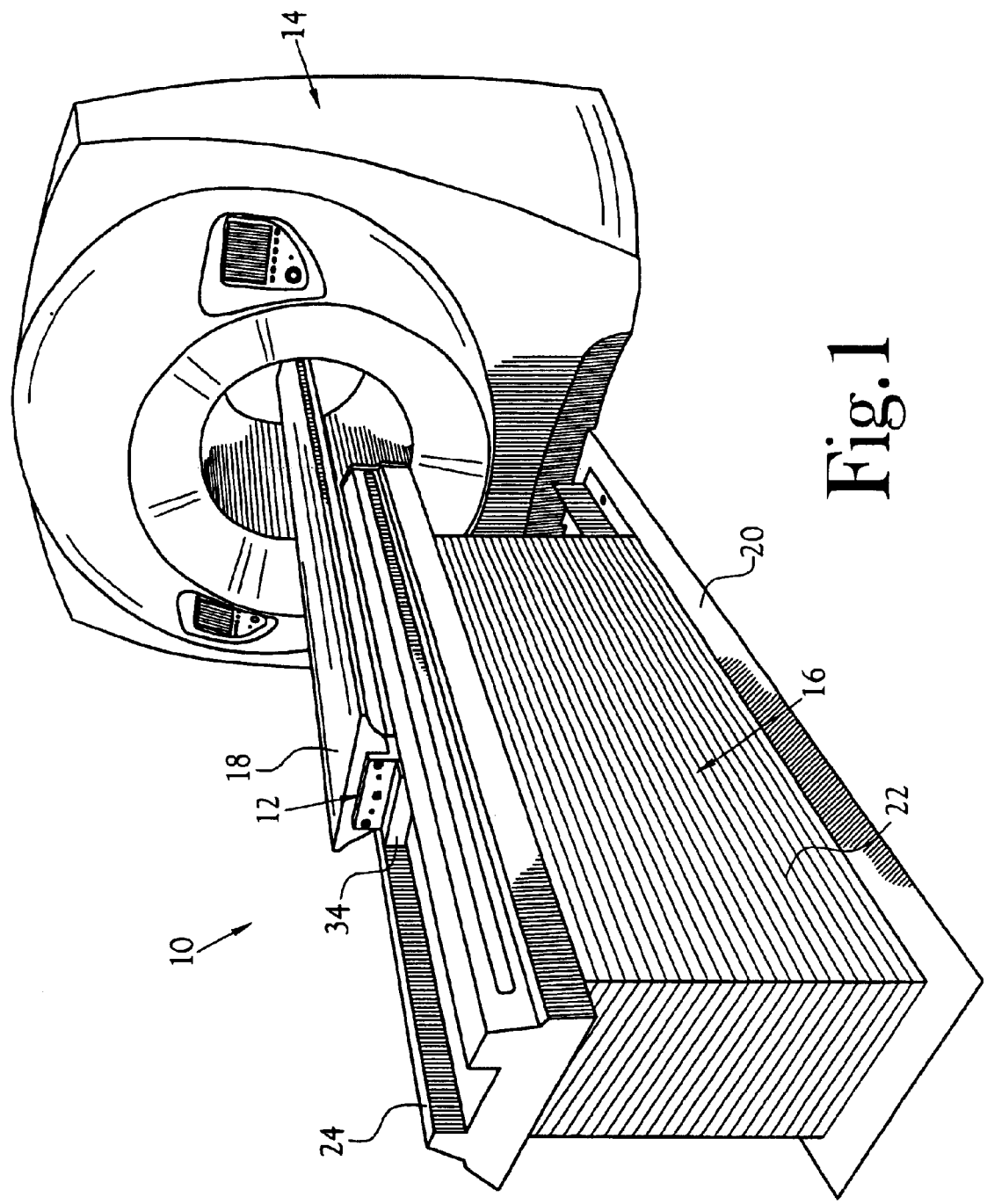
FIG. 1 is a perspective view of a patient handling system of the present invention.
Figure 2:
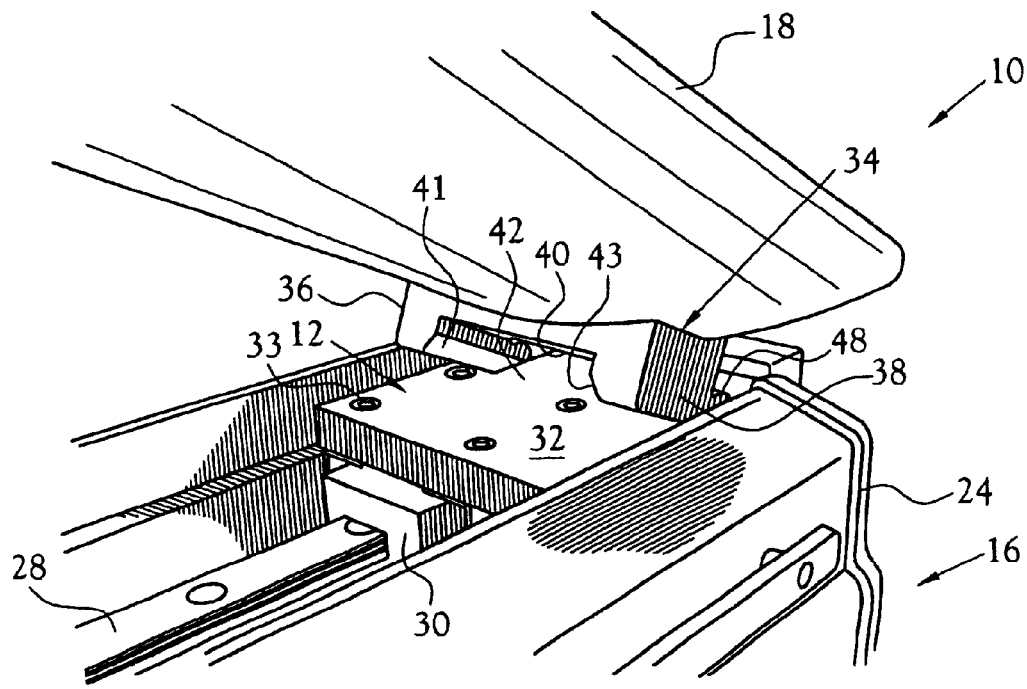
FIG. 2 is a partial perspective view of a patient handling system of the present invention.

A patient handling system for use with positron emission tomography (PET) scanners, computed tomography (CT) scanners, and other imaging, and radiation therapy, devices is illustrated generally at 10 in the drawings. An associated pallet mounting apparatus for releasably mounting, and safely securing, a pallet which supports a patient during a medical imaging procedure is illustrated generally at 12 in FIGS. 1–8. Whereas the patient handling system 10 is illustrated as being used for positioning a patient within the gantry of a PET scanner 14, it will be understood that the system 10 can be used with various medical imaging and therapy devices, and is particularly useful where the patient handling system is to be used for supporting a patient during different types of imaging or radiation therapy procedures, or used with different types of imaging or radiation therapy devices.

The patient handling system 10 includes a pallet support assembly 16 that releasably supports a pallet 18 on which a patient is positioned during a scanning or therapy procedure. In the illustrated embodiment of the patient handling system 10, the pallet support assembly includes a base 20 on which is mounted a height adjustment mechanism 22 for selectively adjusting the vertical position of the pallet 18. Further, a rail assembly 24 is mounted on the mechanism 22 for slidably supporting the pallet 18 such that the pallet 18 can be extended into the field of view of the detectors of the imaging device 14. Accordingly, a patient supported on the pallet 18 can be selectively moved into, and out of the field of view of the detectors, and a patient can be positioned within the gantry of the imaging device 14 to place selected portions of the patient's body within the field of view of the detectors. In order to facilitate the extending and retracting movement of the pallet 18, the rail assembly 24 includes a rail 28 and a carriage 30 (see FIGS. 2 and 4) on which the pallet 18 is supported. The carriage 30 travels along the rail 28, and such movement of the carriage 30 results in horizontal movement of the pallet 18 along the path of the rail 28. Accordingly, the pallet support assembly 16 accommodates both vertical and horizontal movement of the pallet 18 to facilitate the proper positioning of the patient within the field of view of the detectors of the imaging device. It will be understood by those of ordinary skill in the art, however, that the illustrated pallet support assembly 16 is merely representative of one preferred embodiment of a suitable pallet support assembly which can be used in conjunction with the pallet mounting apparatus 12 of the present invention. For example, it is contemplated that the pallet mounting apparatus 12 can be used with patient handling systems wherein the movement of the pallet into the field of view of the detectors is accomplished through movement of the entire patient handling system rather than by extending of the pallet.

As illustrated in FIGS. 2–8, the pallet mounting apparatus 12 includes two interlocking members, one being a base member 32 which is secured to the pallet support assembly 16, and the other being a pallet engaging member 34. More specifically, in the preferred illustrated embodiment the base member 32 is secured to the carriage 30 with suitable fasteners 33, such that the base member 32 moves with the carriage 30 along the rail 28. In the preferred embodiment the base member 32 is fabricated from aluminum which provides a good strength to weight ratio. However, other strong, durable materials can be used such as, for example, steel or brass. Further, in the preferred illustrated embodiment the pallet engaging member 34 is secured to the pallet 18 with suitable fasteners such that when the pallet engaging member is releasably interlocked with the base member 32, the pallet 18 moves with the carriage 30 along the path of the rail 28. In the preferred embodiment the pallet engaging member 34 is also fabricated from aluminum, but other strong, durable materials can be used such as, for example, steel or brass. In order to facilitate the mounting of the pallet engaging member 34 on the pallet 18, the pallet engaging member 34 is provided with an upwardly disposed mounting flange 35 which is secured to the end of the pallet 18 with suitable fasteners. The pallet engaging member 34 also defines mounting holes 39 for receiving bolts or other suitable fasteners, and defines a pallet support surface 37 which engages and supports a portion of the bottom of the pallet 18.

In order to effect the releasable engagement of the pallet engaging member 34 with the base member 32, the pallet engaging member 34 is provided with first and second downwardly extending detention arms 36 and 38, respectively. The detention arms 36 and 38 are selectively spaced so as to define a channel 40 therebetween which closely receives a narrowed portion 42 of the base member 32. More specifically, the base member is provided with first and second oppositely disposed receptors 44 and 46, respectively, such that the narrowed portion 42 is defined between the receptors 44 and 46. It will be understood by those skilled in the art that the close reception of the narrowed portion 42 in the channel 40 restricts lateral, or rotational, movement of the pallet engaging member 34 relative to the base member 32 in a horizontal plane, thereby restricting lateral movement of the pallet 18 relative to the pallet support assembly 16.

Figure 3:
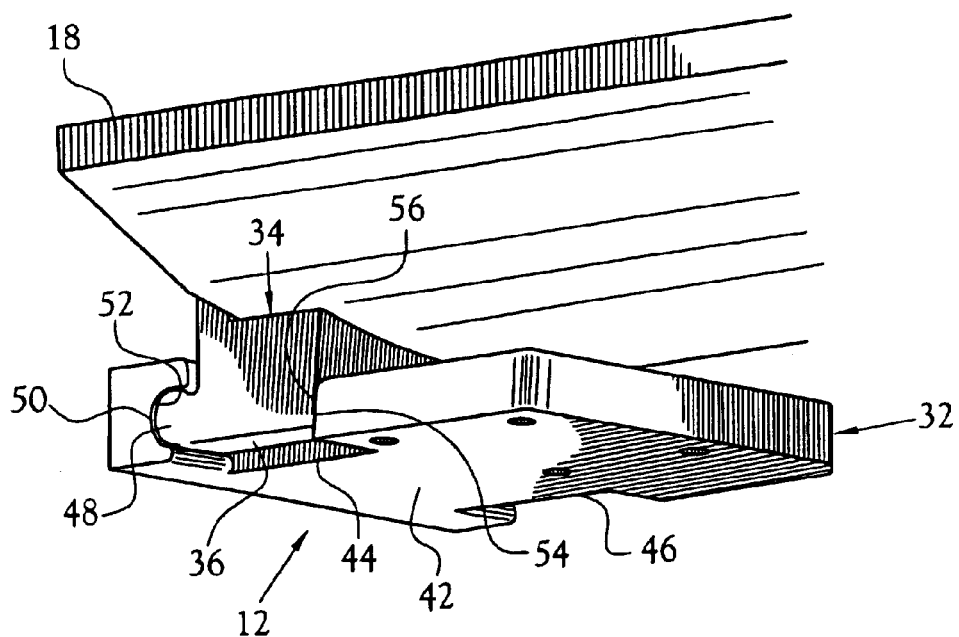
FIG. 3 is a perspective view of a pallet mounting apparatus of the present invention.
Figure 4:
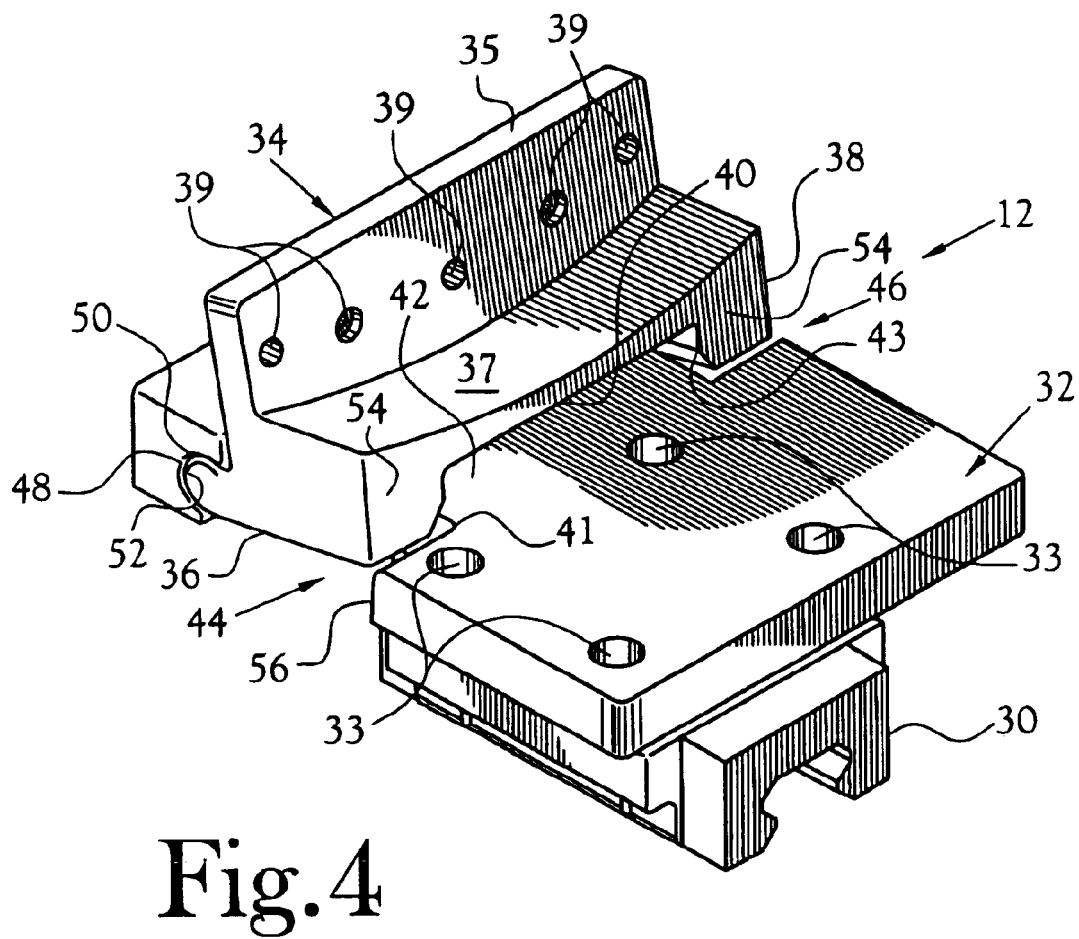
FIG. 4 is a perspective view of a pallet mounting apparatus of the present invention.
Figure 5:
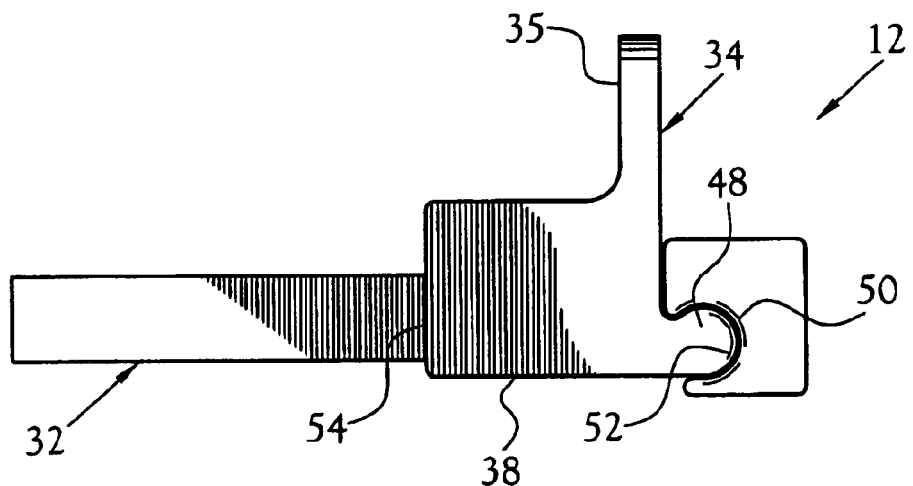
FIG. 5 is a side elevation view of a pallet mounting apparatus of the present invention.
Figure 6:
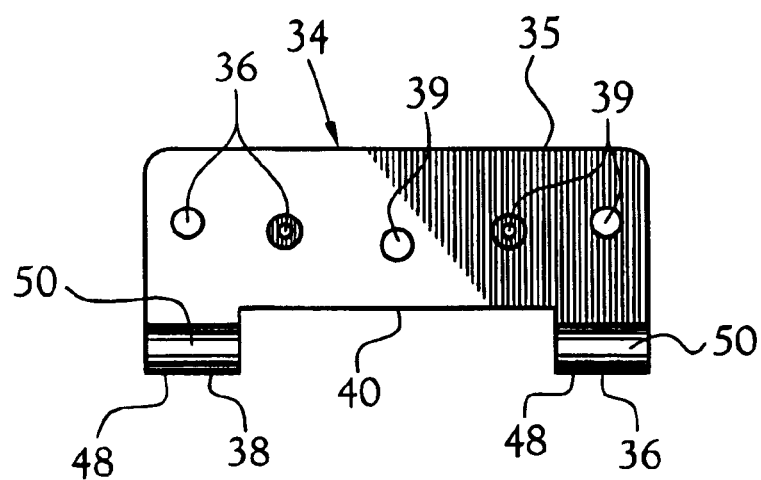
FIG. 6 is a rear elevation view of a pallet mounting apparatus of the present invention.
Figure 7:
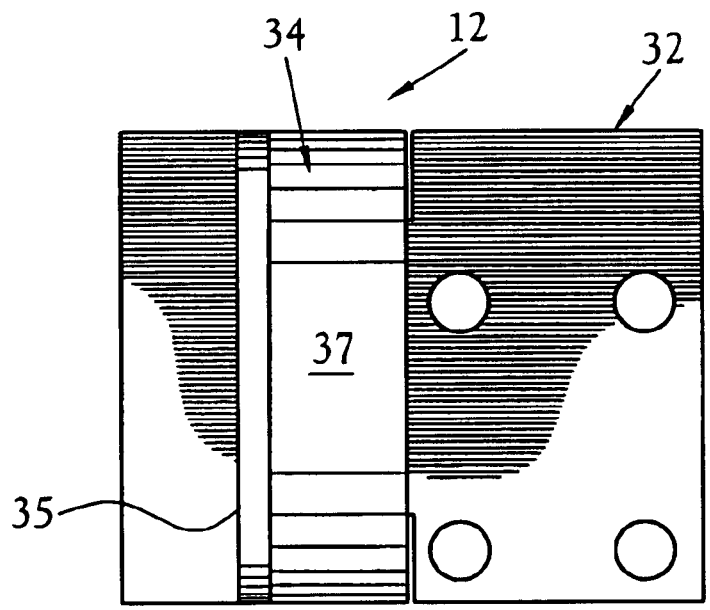
FIG. 7 is a top plan view of a pallet mounting apparatus of the present invention.

Further, the detention arms 36 and 38 are each provided with a rearwardly disposed detent 48 defining an arcuate bearing surface 50. As illustrated in FIGS. 3–4, the detents 48 are releasably and rotatably received in detent receptors 52 defined by the receptors 44 and 46 of the base portion 32.

This rotatable engagement of the pallet engaging member 34 with the base member 32 allows the pallet engaging member 34 to be vertically pivoted about the common axes of the bearing surfaces 50 in order to free the detention arms 36 and 38 from their respective receptors 44 and 46, and such that the pallet engaging member can be disengaged from the base member 32.

Figure 8:
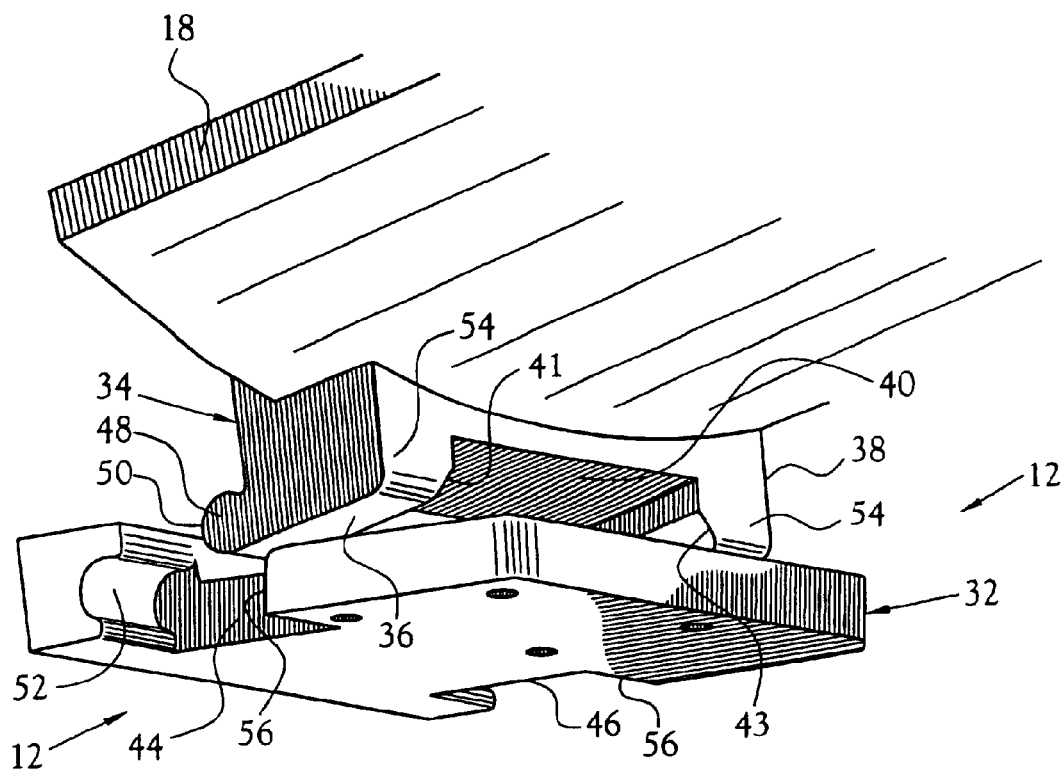
FIG. 8 is a perspective view of a pallet mounting apparatus of the present invention.
Figure 9:
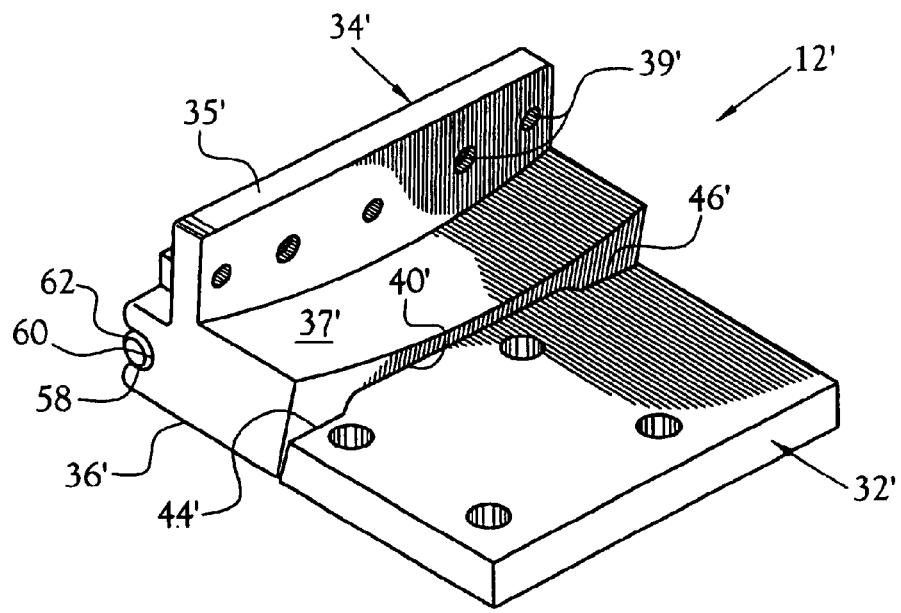
FIG. 9 is a perspective view of a first alternate embodiment of the pallet mounting apparatus of the present invention.

In light of the above, and as illustrated in FIGS. 4 and 8, it will be understood that the pallet 18 is removed from the pallet support assembly 16 by simply pivoting the pallet 18, and, thus, the pallet engaging member 34, vertically until the forward wall surfaces 54 of the detention arms 36 and 38 clear the forward walls 56 of the receptors 44 and 46. The pallet 18 is then removed from the pallet support assembly 16 by lifting the detention arms 36 and 38 from the receptors 44 and 46. To reinstall the pallet 18, or a pallet with a different configuration which is provided with a pallet engaging member 34, the detents 48 are positioned in their associated detent receptors 52, and the pallet is pivoted downwardly to lock the detention arms 36 and 38 in the receptors 44 and 46. It will be noted that in order to facilitate the installation of a pallet 18, the opposite side walls which define the channel 40 are provided with beveled portions 41 and 43 which serve to guide the narrowed portion 42 of the base member 32 into the channel 40.

As noted above, the close fit of the detention arms 36 and 38 in the receptors 44 and 46 prohibits lateral or rotational movement of the pallet 18 in a horizontal plane relative to the pallet support assembly 16. It will also be noted that when the detention arms 36 and 38 are interlocked in the receptors 44 and 46, the forward walls 56 of the receptors 44 and 46 serve as stops which engage the forward wall surfaces 54 of the detention arms 36 and 38 to prohibit longitudinal movement of the pallet engaging member 34, and, thus, longitudinal movement of the pallet 18, relative to the pallet support assembly 16. Accordingly, it will be appreciated that the apparatus 12 allows various pallets, such as the pallets 18 and 18' (See FIG. 14), to be interchangeably used with the same pallet support assembly 16. Although releasably mounted, each pallet is held firmly in position on the pallet support assembly 16 such that inadvertent movement of the pallet does not compromise the accuracy of medial imaging, or radiation therapy.

In FIGS. 9–12 an alternative embodiment of the apparatus for releasably mounting a pallet of the present invention is illustrated generally at 12'. In the preferred illustrated embodiment the pallet mounting apparatus 12' includes two interlocking members, one being a base member 32' which is secured to the pallet support assembly 16, and the other being a pallet engaging member 34' which is mounted on the pallet 18. In order to facilitate the mounting of the pallet engaging member 34' on the pallet 18, the pallet engaging member 34' is provided with an upwardly disposed mounting flange 35' which is secured to the end of the pallet 18 with suitable fasteners. The pallet engaging member 34' also defines a pallet support surface 37' which engages and supports a portion of the bottom of the pallet 18.

In order to effect the releasable engagement of the pallet engaging member 34' with the base member 32', the pallet engaging member 34' is provided with first and second downwardly extending detention arms 36' and 38', respectively. The detention arms 36' and 38' are selectively spaced so as to define a channel 40' therebetween which closely receives a narrowed portion 42' of the base member 32'. More specifically, the base member is provided with first and second oppositely disposed receptors 44' and 46', respectively, such that the narrowed portion 42' is defined between the receptors 44' and 46'. As with the apparatus 12 described above, the close reception of the narrowed portion 42' of the apparatus 12' in the channel 40' restricts lateral or rotational movement of the pallet engaging member 34' relative to the base member 32' in a horizontal plane, thereby restricting lateral movement of the pallet 18 relative to the pallet support assembly 16.

Figure 10:
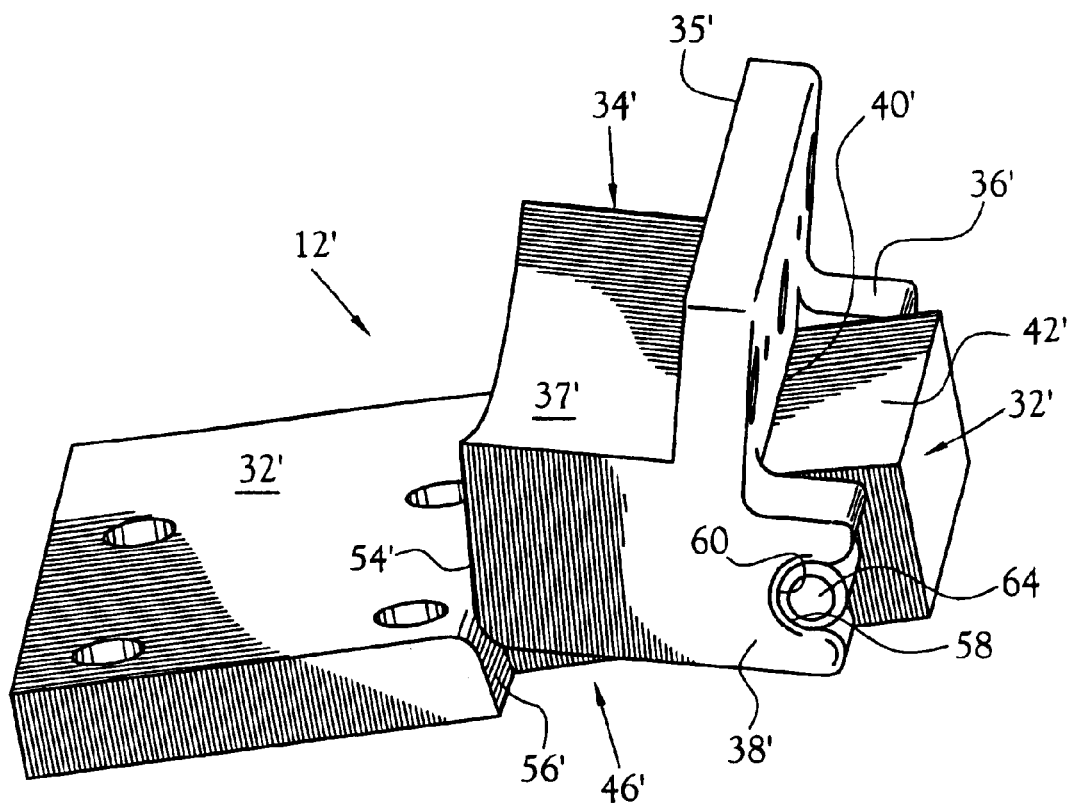
FIG. 10 is a perspective view of the first alternate embodiment of the pallet mounting apparatus of the present invention.
Figure 11:
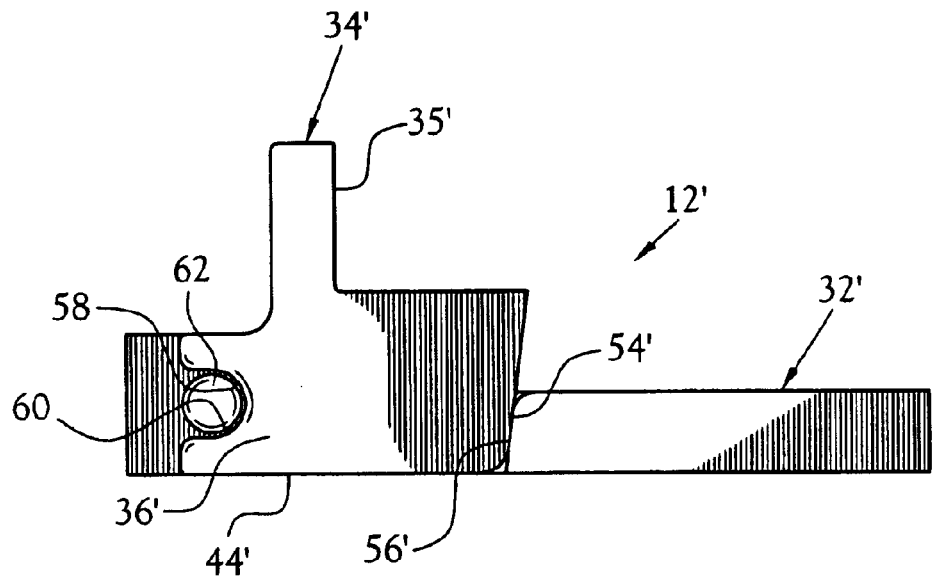
FIG. 11 is a side elevation view of the first alternate embodiment of the pallet mounting apparatus of the present invention.
Figure 12:
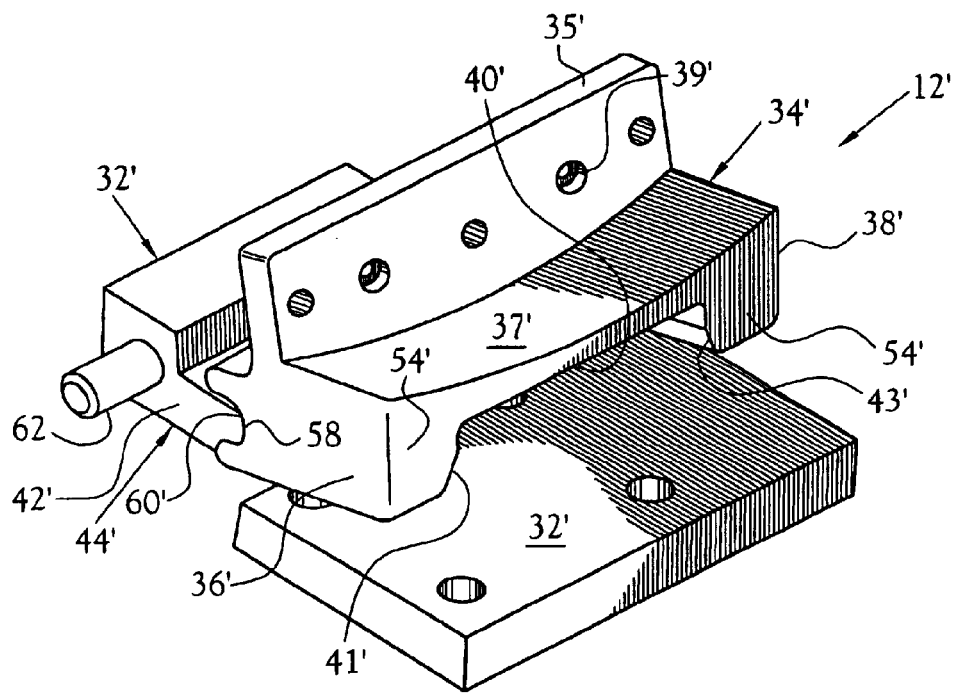
FIG. 12 is a perspective view of the first alternate embodiment of the pallet mounting apparatus of the present invention.

Further, the detention arms 36' and 38' each define a rearwardly disposed annular receptor 58 defining an arcuate surface 60 configured to closely receive one of a pair of oppositely disposed pins 62 and 64 which are mounted on the base member 32' and extend laterally into the receptors 44' and 46', respectively. More specifically, and as illustrated in FIGS. 10–12, the pins 62 and 64 are releasably and rotatably received in the receptors 58. This rotatable engagement of the pallet engaging member 34' with the base member 32' allows the pallet engaging member 34' to be vertically pivoted about the common axes of the pins 62 and 64, and arcuate surfaces 58, in order to free the detention arms 36' and 38' from their respective receptors 44' and 46' such that the pallet engaging member can be disengaged from the base member 32'.

Figure 13:
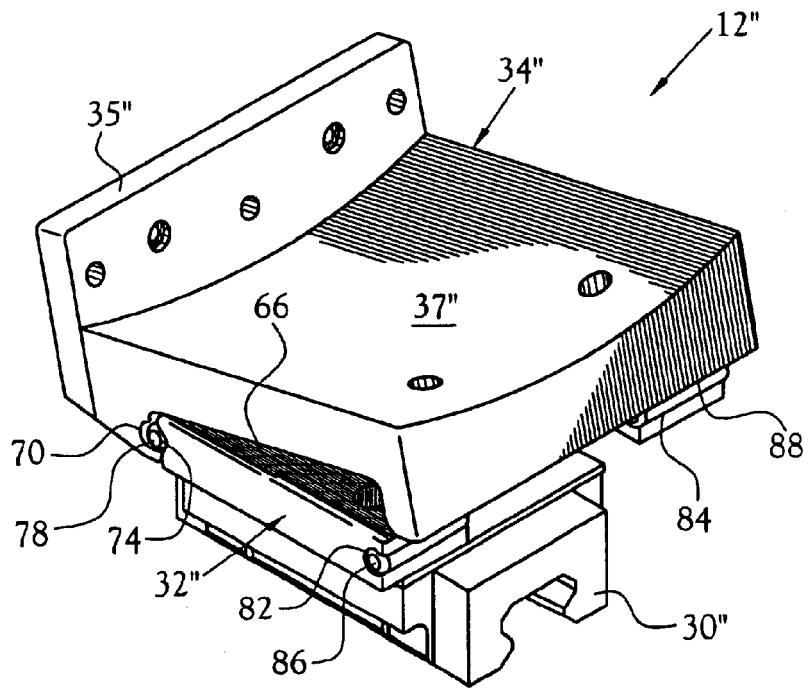
FIG. 13 is a perspective view of a second alternate embodiment of the pallet mounting apparatus of the present invention.
Figure 14:
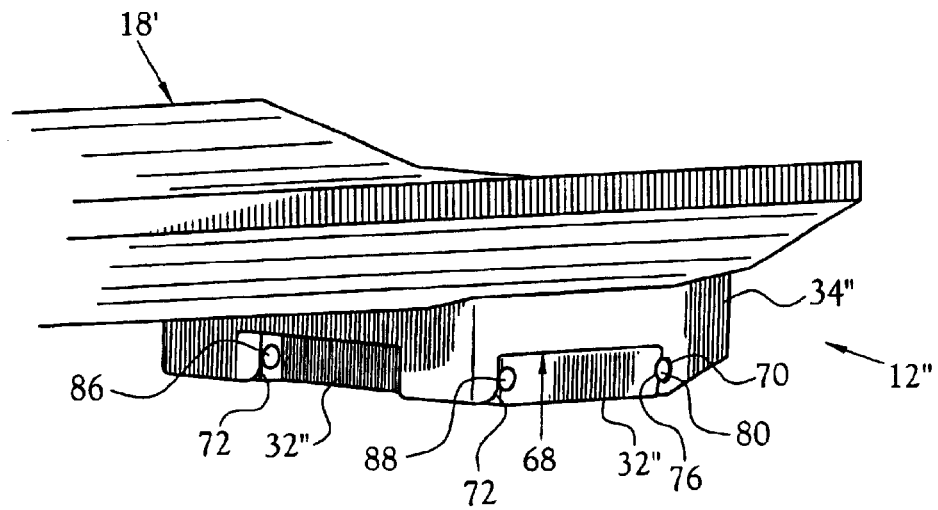
FIG. 14 is a perspective view of the second alternate embodiment of the pallet mounting apparatus of the present invention.
Figure 15:
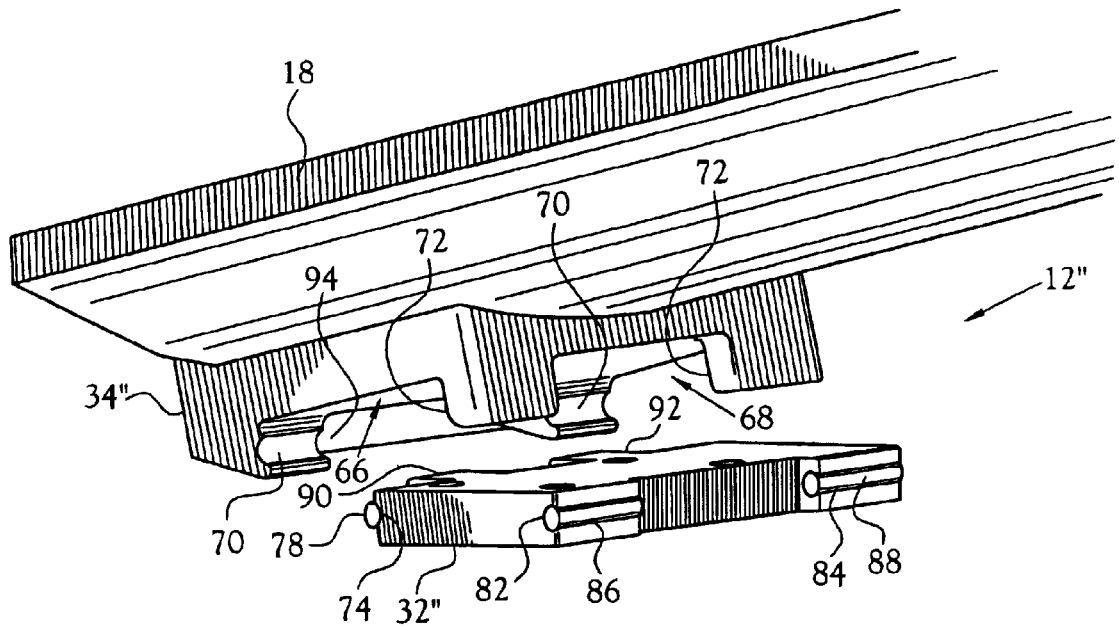
FIG. 15 is a perspective view of the second alternate embodiment of the pallet mounting apparatus of the present invention.

In FIGS. 13–15 another alternative embodiment of the pallet mounting apparatus of the present invention is illustrated generally at 12". In the preferred illustrated embodiment the pallet mounting apparatus 12" includes two interlocking members, one being a base member 32" which is secured to the pallet support assembly 16, and the other being a pallet engaging member 34" which is mounted on the pallet 18'. In order to facilitate the mounting of the pallet engaging member 34" on the pallet 18', the pallet engaging member 34" is provided with an upwardly disposed mounting flange 35" which is secured to the end of the pallet 18' with suitable fasteners. The pallet engaging member 34" also defines a pallet support surface 37" which engages and supports a portion of the bottom of the pallet 18'.

In order to effect the releasable engagement of the pallet engaging member 34" with the base member 32", the pallet engaging member 34" is provided with a pair of receptors 66 and 68 for releasably receiving the base member 32". Each of the receptors 66 and 68 defines a rearwardly disposed bearing receptor 70, and a forward retaining surface 72. Further, the base member 32" defines a pair of rearwardly disposed bearing holders 74 and 76 in which a pair of bearings 78 and 80 are mounted, and also defines a pair of forwardly disposed bearing holders 82 and 84, in which a pair of bearings 86 and 88 are mounted. As illustrated in FIGS. 13 and 14, when the base member 32" and pallet engaging member 34" are interlocked the bearings 78 and 80 of the base member 32" are positioned in the bearing receptors 70 of the pallet engaging member 34". It will also be noted that the forward retaining surfaces 72 of the receptors 66 and 68 engage the bearings 86 and 88 such that the base member 32" is held firmly in the receptors 66 and 68, and such that longitudinal movement of the pallet engaging member 34" relative to the base member 32" is restricted. Further, in order to restrict lateral movement of the pallet engaging member 34" relative to the base member 32", the base member 32" is provided with a pair of rearwardly extending stop members 90 and 92 which are closely received in a channel 94 defined by the pallet engaging member 34".

In order to release the pallet 18' from the pallet support assembly 16 when using the apparatus 12", the pallet, and, thus, the pallet support member 34", is pivoted vertically about the common axes of the bearings 78 and 80 until the forward retaining surfaces 72 of the receptors 66 and 68 no longer restrict movement of the base member 32" relative to the pallet engaging member 34". The pallet support member 34" is then moved rearwardly to free the bearings 78 and 80 from the bearing receptors 70, allowing the pallet 18' to be lifted away from the pallet support assembly 16. In order to reinstall the pallet 18', or another pallet having a different configuration, the pallet 18' and pallet engaging member 34" are lowered, at an angle, on to the base member 32" such that the rear bearings 78 and 80 are positioned in the bearing receptors 70. The pallet and pallet engaging member 34" are then pivoted into a horizontal position such that the forward retaining surfaces 72 serve to prohibit longitudinal movement of the base member 32" in the receptors 66 and 68.

In light of the above, it will be recognized that the pallet mounting apparatus of the present invention, in its various embodiments 12, 12' and 12", allows pallets, such as the pallets 18 and 18' to be quickly, and easily, removed and reinstalled on a pallet support assembly 16. Moreover, when one of the base members 32, 32' and 32", is interlocked with one of the pallet engaging members 34, 34' and 34", the pallet 18 is held in a stable position to insure the safety of the patient, and such that inadvertent movement of the pallet 18 does not compromise the imaging or therapy procedure being performed.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, we claim:

1. A patient handling system for supporting a patient during a medical procedure, said patient handling system comprising:
   a pallet for supporting a patient;
   a pallet support assembly for supporting said pallet and for selectively positioning said pallet, and a patient supported thereon, relative to a medical imaging/therapy device;
   a pallet mounting apparatus for releasably mounting said pallet on said pallet support assembly, said pallet mounting apparatus including a first interlocking member mounted on said pallet support assembly, and a second interlocking member mounted on said pallet for releasably interlocking with said first interlocking member, said second interlocking member of said pallet mounting apparatus being provided with first and second downwardly extending detention arms for releasably interlocking with said first interlocking member, said first interlocking member of said pallet mounting apparatus defining first and second detention arm receptors for releasably receiving said first and second downwardly extending detention arms, respectively, whereby said first interlocking member is releasably interlocked with said second interlocking member to releasably secure said pallet on said pallet support assembly, said first and second detention arms of said second interlocking member being selectively spaced so as to define a channel therebetween, said first interlocking member defining a narrowed portion for being closely received in said channel when said first and second interlocking members are interlocked, whereby the close reception of said narrowed portion of said first interlocking member in said channel of said second interlocking member restricts lateral movement of said second interlocking member relative to said first interlocking member, wherein relative movement between said first interlocking member and said second interlocking member in a horizontal plane is substantially prohibited when said first and second interlocking members are interlocked, and wherein selective vertical pivoting of said second interlocking member relative to said first interlocking member permits selective disengagement of said second interlocking member from said first interlocking member to facilitate release of said pallet from said pallet support assembly.

2. The patient handling system of claim 1 wherein each said first and second detention arm is provided with a detent defining an arcuate bearing surface, and wherein each said first and second detention arm receptor of said first interlocking member defines a detent receptor for rotatably receiving one said detent, whereby said second interlocking member can be vertically pivoted about the axes of said arcuate surfaces of said detents to effect release of said first and second detention arms from said first and second detention arm receptors, and whereby said pallet can be removed from said pallet support assembly.

3. The patient handling system of claim 2 wherein each said first and second detention arm defines a forward wall surface, and wherein each said first and second detention arm receptor defines a forward wall for releasably engaging one said forward wall surface, whereby longitudinal movement of said pallet relative to said pallet support assembly is substantially restricted.

4. The patient handling system of claim 1 wherein each said first and second detention arm defines a rearwardly disposed annular receptor having an arcuate surface, and wherein each said first and second receptor of said first interlocking member is provided with an outwardly projecting pin for being rotatably received in one said annular receptor, whereby said second interlocking member can be vertically pivoted about the axes of said outwardly projecting pins of said first interlocking member to effect release of said first and second detention arms from said first and second detention arm receptors, and whereby said pallet can be removed from said pallet support assembly.

5. A patient handling system for supporting a patient during a medical procedure, said patient handling system comprising:
   a pallet for supporting a patient;
   a pallet support assembly for supporting said pallet and for selectively positioning said pallet, and a patient supported thereon, relative to a medical imaging/therapy device;
   a pallet mounting apparatus for releasably mounting said pallet on said pallet support assembly, said pallet mounting apparatus including a first interlocking member mounted on said pallet support assembly, and a second interlocking member mounted on said pallet for releasably interlocking with said first interlocking member, said second interlocking member of said pallet mounting apparatus being provided with first and second downwardly extending detention arms for releasably interlocking with said first interlocking member, wherein each said first and second detention arm is provided with a detent defining an arcuate bearing surface, said first interlocking member of said pallet mounting apparatus defining first and second detention arm receptors for releasably receiving said first and second downwardly extending detention arms, respectively, whereby said first interlocking member is releasably interlocked with said second interlocking member to releasably secure said pallet on said pallet support assembly, wherein each said first and second detention arm receptor of said first interlocking member defines a detent receptor for rotatably receiving one said detent, whereby said second interlocking member can be vertically pivoted about the axes of said arcuate surfaces of said detents to effect release of said first and second detention arms from said first and second detention arm receptors, and whereby said pallet can be removed from said pallet support assembly, wherein relative movement between said first interlocking member and said second interlocking member in a horizontal plane is substantially prohibited when said first and second interlocking members are interlocked, and wherein selective vertical pivoting of said second interlocking member relative to said first interlocking member permits selective disengagement of said second interlocking member from said first interlocking member to facilitate release of said pallet from said pallet support assembly.

6. A patient handling system for supporting a patient during a medical procedure, said patient handling system comprising:

a pallet for supporting a patient;

a pallet support assembly for supporting said pallet and for selectively positioning said pallet, and a patient supported thereon, relative to a medical imaging/therapy device;

a pallet mounting apparatus for releasably mounting said pallet on said pallet support assembly, said pallet mounting apparatus including a first interlocking member mounted on said pallet support assembly, and a second interlocking member mounted on said pallet for releasably interlocking with said first interlocking member, said second interlocking member of said pallet mounting apparatus being provided with first and second downwardly extending detention arms for releasably interlocking with said first interlocking member, said first interlocking member of said pallet mounting apparatus defining first and second detention arm receptors for releasably receiving said first and second downwardly extending detention arms, respectively, whereby said first interlocking member is releasably interlocked with said second interlocking member to releasably secure said pallet on said pallet support assembly, each said first and second detention arm defining a rearwardly disposed annular receptor having an arcuate surface, each said first and second receptor of said first interlocking member being provided with an outwardly projecting pin for being rotatably received in one said annular receptor, whereby said second interlocking member can be vertically pivoted about the axes of said outwardly projecting pins of said first interlocking member to effect release of said first and second detention arms from said first and second detention arm receptors, and whereby said pallet can be removed from said pallet support assembly, wherein relative movement between said first interlocking member and said second interlocking member in a horizontal plane is substantially prohibited when said first and second interlocking members are interlocked, and wherein selective vertical pivoting of said second interlocking member relative to said first interlocking member permits selective disengagement of said second interlocking member from said first interlocking member to facilitate release of said pallet from said pallet support assembly.

7. A patient handling system for supporting a patient during a medical procedure, said patient handling system comprising:

a pallet for supporting a patient;

a pallet support assembly for supporting said pallet and for selectively positioning said pallet, and a patient supported thereon, relative to a medical imaging/therapy device;

a pallet mounting apparatus for releasably mounting said pallet on said pallet support assembly, said pallet mounting apparatus including a first interlocking member mounted on said pallet support assembly, and a second interlocking member mounted on said pallet for releasably interlocking with said first interlocking member, said second interlocking member defining first and second receptors for releasably receiving said first interlocking member, each said first and second receptor defining a rearwardly disposed bearing receptor, said first interlocking member being provided with first and second rearwardly disposed bearings for being rotatably received in said bearing receptors, whereby said second interlocking member can be vertically pivoted about the axes of said bearings of said first interlocking member to effect release of said first interlocking member from said second interlocking member, and whereby said pallet can be removed from said pallet support assembly, wherein relative movement between said first interlocking member and said second interlocking member in a horizontal plane is substantially prohibited when said first and second interlocking members are interlocked, and wherein selective vertical pivoting of said second interlocking member relative to said first interlocking member permits selective disengagement of said second interlocking member from said first interlocking member to facilitate release of said pallet from said pallet support assembly.

8. The patient handling system of claim 7 wherein each said first and second receptor of said second interlocking member defines a forward retaining surface, and said first interlocking member is provided with first and second forwardly disposed bearings for releasably engaging said forward retaining surfaces of said first and second receptors as said first interlocking member and said second interlocking member are interlocked.

9. A pallet mounting apparatus for releasably mounting a pallet for supporting a patient on a pallet support assembly of a patient handling system, said apparatus comprising a first interlocking member mounted on the pallet support assembly, and a second interlocking member mounted on the pallet for releasably interlocking with said first interlocking member, said second interlocking member being provided with first and second downwardly extending detention arms for releasably interlocking with said first interlocking member, said first interlocking member defining first and second detention arm receptors for releasably receiving said first and second downwardly extending detention arms, respectively, whereby said first interlocking member is releasably interlocked with said second interlocking member to releasably secure the pallet on the pallet support assembly, wherein said first and second detention arms of said second interlocking member are selectively spaced so as to define a channel therebetween, and wherein said first interlocking member defines a narrowed portion for being closely received in said channel when said first and second interlocking members are interlocked, whereby the close reception of said narrowed portion of said first interlocking member in said channel of said second interlocking member restricts lateral movement of said second interlocking member relative to said first interlocking member, wherein relative movement between said first interlocking member and said second interlocking member in a horizontal plane is substantially prohibited when said first and second interlocking members are interlocked, and wherein selective vertical pivoting of said second interlocking member relative to said first interlocking member permits selective disengagement of said second interlocking member from said first interlocking member to facilitate release of the pallet from the pallet support assembly.

10. The pallet mounting apparatus of claim 9 wherein each said first and second detention arm is provided with a detent defining an arcuate bearing surface, and wherein each said first and second detention arm receptor of said first interlocking member defines a detent receptor for rotatably receiving one said detent, whereby said second interlocking member can be vertically pivoted about the axes of said arcuate surfaces of said detents to effect release of said first and second detention arms from said first and second detention arm receptors, and whereby the pallet can be removed from the pallet support assembly.

11. The pallet mounting apparatus of claim 10 wherein said first and second detention arms define forward wall surfaces, and wherein said first and second detention arm receptors define forward walls for releasably engaging said forward wall surfaces, whereby longitudinal movement of the pallet relative to the pallet support assembly is substantially restricted.

12. The pallet mounting apparatus of claim 9 wherein each said first and second detention arm defines a rearwardly disposed annular receptor having an arcuate surface, and wherein each said first and second receptor of said first interlocking member is provided with an outwardly projecting pin for being rotatably received in one said annular receptor, whereby said second interlocking member can be vertically pivoted about the axes of said outwardly projecting pins of said first interlocking member to effect release of said first and second detention arms from said first and second detention arm receptors, and whereby the pallet can be removed from the pallet support assembly.

13. A pallet mounting apparatus for releasably mounting a pallet for supporting a patient on a pallet support assembly of a patient handling system, said apparatus comprising a first interlocking member mounted on the pallet support assembly, and a second interlocking member mounted on the pallet for releasably interlocking with said first interlocking member, said second interlocking member being provided with first and second downwardly extending detention arms for releasably interlocking with said first interlocking member, said first interlocking member defining first and second detention arm receptors for releasably receiving said first and second downwardly extending detention arms, respectively, whereby said first interlocking member is releasably interlocked with said second interlocking member to releasably secure the pallet on the pallet support assembly, wherein each said first and second detention arm is provided with a detent defining an arcuate bearing surface, and wherein each said first and second detention arm receptor of said first interlocking member defines a detent receptor for rotatably receiving one said detent, whereby said second interlocking member can be vertically pivoted about the axes of said arcuate surfaces of said detents to effect release of said first and second detention arms from said first and second detention arm receptors, and whereby the pallet can be removed from the pallet support assembly, wherein relative movement between said first interlocking member and said second interlocking member in a horizontal plane is substantially prohibited when said first and second interlocking members are interlocked, and wherein selective vertical pivoting of said second interlocking member relative to said first interlocking member permits selective disengagement of said second interlocking member from said first interlocking member to facilitate release of the pallet from the pallet support assembly.

14. A pallet mounting apparatus for releasably mounting a pallet for supporting a patient on a pallet support assembly of a patient handling system, said apparatus comprising a first interlocking member mounted on the pallet support assembly, and a second interlocking member mounted on the pallet for releasably interlocking with said first interlocking member, said second interlocking member being provided with first and second downwardly extending detention arms for releasably interlocking with said first interlocking member, said first interlocking member defining first and second detention arm receptors for releasably receiving said first and second downwardly extending detention arms, respectively, whereby said first interlocking member is releasably interlocked with said second interlocking member to releasably secure the pallet on the pallet support assembly, wherein each said first and second detention arm defines a rearwardly disposed annular receptor having an arcuate surface, and wherein each said first and second receptor of said first interlocking member is provided with an outwardly projecting pin for being rotatably received in one said annular receptor, whereby said second interlocking member can be vertically pivoted about the axes of said outwardly projecting pins of said first interlocking member to effect release of said first and second detention arms from said first and second detention arm receptors, and whereby the pallet can be removed from the pallet support assembly, wherein relative movement between said first interlocking member and said second interlocking member in a horizontal plane is substantially prohibited when said first and second interlocking members are interlocked, and wherein selective vertical pivoting of said second interlocking member relative to said first interlocking member permits selective disengagement of said second interlocking member from said first interlocking member to facilitate release of the pallet from the pallet support assembly.

15. A pallet mounting apparatus for releasably mounting a pallet for supporting a patient on a pallet support assembly of a patient handling system, said apparatus comprising a first interlocking member mounted on the pallet support assembly, and a second interlocking member mounted on the pallet for releasably interlocking with said first interlocking member, said second interlocking member of said pallet mounting apparatus defining first and second receptors for releasably receiving said first interlocking member, wherein relative movement between said first interlocking member and said second interlocking member in a horizontal plane is substantially prohibited when said first and second interlocking members are interlocked, and wherein selective vertical pivoting of said second interlocking member relative to said first interlocking member permits selective disengagement of said second interlocking member from said first interlocking member to facilitate release of the pallet from the pallet support assembly.

16. The pallet mounting apparatus of claim 15 wherein each said first and second receptor of said second interlocking member defines a rearwardly disposed bearing receptor, and wherein said first interlocking member is provided with first and second rearwardly disposed bearings for being rotatably received in said bearing receptors, whereby said second interlocking member can be vertically pivoted about the axes of said first and second rearwardly disposed bearings of said first interlocking member to effect release of said first interlocking member from said second interlocking member, and whereby the pallet can be removed from the pallet support assembly.

17. The pallet mounting apparatus of claim 16 wherein each said first and second receptor of said second interlocking member defines a forward retaining surface, and said first interlocking member is provided with first and second forwardly disposed bearings for releasably engaging said forward retaining surfaces of said first and second receptors as said first interlocking member and said second interlocking members are interlocked.

18. A pallet mounting apparatus for releasably mounting a pallet for supporting a patient on a pallet support assembly of a patient handling system, said apparatus comprising a base member mounted on the pallet support assembly, and a pallet engaging member mounted on the pallet for releasably interlocking with said base member, said pallet engaging member being provided with first and second downwardly extending detention arms, and said base member defining first and second detention arm receptors for releasably receiving said first and second downwardly extending detention arms, respectively, whereby said base member is releasably interlocked with said pallet engaging member to releasably secure the pallet on the pallet support assembly, each said first and second detention arm being provided with a detent defining an arcuate bearing surface, each said first and second detention arm receptor of said first interlocking member defining a detent receptor for rotatably receiving one said detent, whereby said pallet engaging member can be vertically pivoted about the axes of said arcuate surfaces of said detents to effect release of said first and second detention arms from said first and second detention arm receptors, and whereby the pallet can be removed from the pallet support assembly.

* * * * *